(12) United States Patent
Doll et al.

(10) Patent No.: US 12,274,493 B2
(45) Date of Patent: Apr. 15, 2025

(54) COMBINATION ELECTROSURGICAL AND MECHANICAL RESECTION DEVICE

(71) Applicants: Smith & Nephew, Inc., Memphis, TN (US); Smith & Nephew Orthopaedics AG, Zug (CH); Smith & Nephew Asia Pacific Pte Limited, Singapore (SG)

(72) Inventors: Sean Doll, Cedar Park, TX (US); Bob Lathrop, Lawrence, MA (US); Craig Di-Stefano, Andover, MA (US)

(73) Assignees: Smith & Nephew, Inc., Memphis, TN (US); Smith & Nephew Orthopaedics AG, Zug (CH); Smith & Nephew Asia Pacific Pte Limited, Singapore (SG)

( * ) Notice: Subject to any disclaimer, the term of this patent is extended or adjusted under 35 U.S.C. 154(b) by 849 days.

(21) Appl. No.: 17/433,026

(22) PCT Filed: Feb. 24, 2020

(86) PCT No.: PCT/US2020/019479
§ 371 (c)(1),
(2) Date: Aug. 23, 2021

(87) PCT Pub. No.: WO2020/172659
PCT Pub. Date: Aug. 27, 2020

(65) Prior Publication Data
US 2022/0160425 A1 May 26, 2022

Related U.S. Application Data

(60) Provisional application No. 62/853,972, filed on May 29, 2019, provisional application No. 62/809,286, filed on Feb. 22, 2019.

(51) Int. Cl.
*A61B 18/12* (2006.01)
*A61B 18/16* (2006.01)
(Continued)

(52) U.S. Cl.
CPC .......... *A61B 18/16* (2013.01); *A61B 18/1206* (2013.01); *A61B 2018/00077* (2013.01);
(Continued)

(58) Field of Classification Search
CPC .... A61B 17/32002; A61B 2017/00477; A61B 18/1206; A61B 18/148; A61B 18/16;
(Continued)

(56) References Cited

U.S. PATENT DOCUMENTS 6,827,725 B2 12/2004 Batchelor et al.
2013/0345704 A1 12/2013 Palmer et al.
(Continued)

FOREIGN PATENT DOCUMENTS

WO 18183002 A1 10/2018

OTHER PUBLICATIONS

Search Report and Written Opinion for PCT/US2020/019479 dated Jul. 28, 2020.

*Primary Examiner* — Khadijeh A Vahdat
(74) *Attorney, Agent, or Firm* — Norman F. Hainer, Jr.; Kate Ryland Tetzlaff

(57) ABSTRACT

A combination medical device for removing and treating tissue in a patient is disclosed. The device includes a reusable handle and a blade selectively connectable to the handle. The blade includes an outer sleeve having a lumen with an inner shaft disposed therein. The inner shaft may be coupled to a motor drive unit disposed within the handle and may rotate so as to mechanically cut tissue as the inner shaft rotates. The outer sleeve includes at least one electrode for electrosurgically treating tissue. The reusable handle includes at least one control switch for controlling a parameter associated with the rotation of the inner shaft. The blade also may include a switch assembly in electrical communication with the at least one electrode, the switch assembly
(Continued)

including attachment means for selective attachment of the switch assembly to the reusable handle.

20 Claims, 11 Drawing Sheets

(51) Int. Cl.
　　*A61B 18/00*　　(2006.01)
　　*A61B 18/14*　　(2006.01)
(52) U.S. Cl.
　　CPC ............... *A61B 2018/00083* (2013.01); *A61B 2018/00208* (2013.01); *A61B 2018/00577* (2013.01); *A61B 2018/00589* (2013.01); *A61B 2018/00601* (2013.01); *A61B 2018/00744* (2013.01); *A61B 2018/00791* (2013.01); *A61B 2018/00916* (2013.01); *A61B 2018/126* (2013.01); *A61B 2018/1412* (2013.01); *A61B 2018/162* (2013.01); *A61B 2218/007* (2013.01)

(58) Field of Classification Search
　　CPC ........... A61B 2018/00077; A61B 2018/00083; A61B 2018/00202; A61B 2018/00208; A61B 2018/00577; A61B 2018/00589; A61B 2018/00601; A61B 2018/00744; A61B 2018/00791; A61B 2018/00916; A61B 2018/126; A61B 2018/1412; A61B 2018/162; A61B 2218/007
　　See application file for complete search history.

(56) References Cited

U.S. PATENT DOCUMENTS

| | | |
|---|---|---|
| 2015/0265337 A1 | 9/2015 | Bloom |
| 2016/0235468 A1 | 8/2016 | Prisco |
| 2017/0258519 A1 | 9/2017 | Germain et al. |
| 2018/0213461 A1 | 7/2018 | Grayson et al. |
| 2018/0263649 A1 | 9/2018 | Germain et al. |
| 2019/0059983 A1* | 2/2019 | Germain ............ A61B 17/1606 |
| 2020/0222108 A1 | 7/2020 | Germain et al. |

* cited by examiner

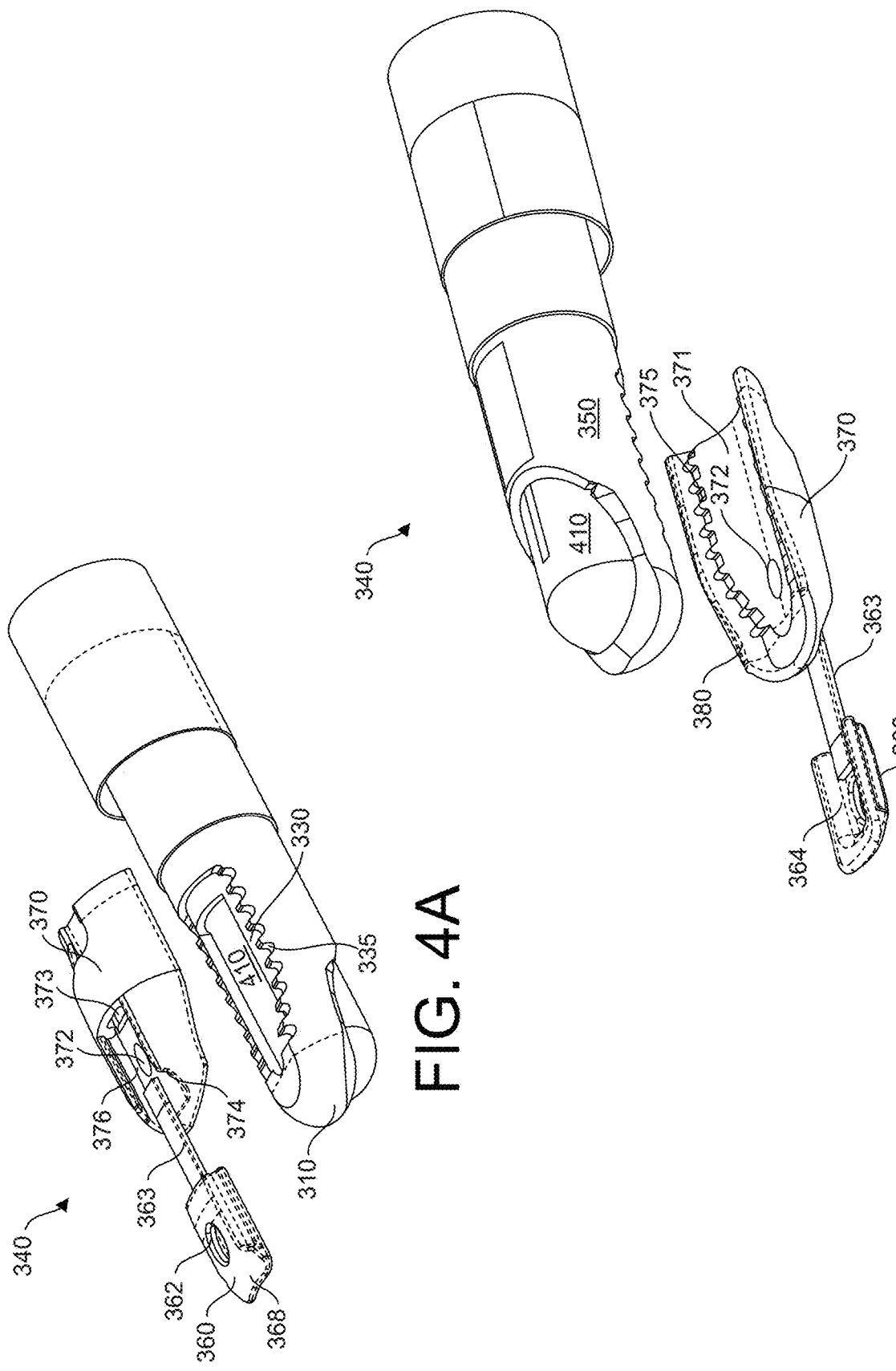

COMBINATION ELECTROSURGICAL AND MECHANICAL RESECTION DEVICE

CROSS-REFERENCE TO RELATED APPLICATIONS

This application is a 371 Application of PCT Application Serial No. PCT/US20/19479 filed Feb. 24, 2020 and titled "COMBINATION ELECTROSURGICAL AND MECHANICAL RESECTION DEVICE", which claims the benefit of U.S. Provisional Application No. 62/853,972 filed May 29, 2019 entitled "COMBINATION ELECTROSURGICAL AND MECHANICAL RESECTION DEVICE", and U.S. Provisional Application No. 62/809,286 filed Feb. 22, 2019 entitled "COMBINATION ELECTROSURGICAL AND MECHANICAL RESECTION DEVICE", the entirety of which is incorporated herein by reference in its entirety.

FIELD OF THE INVENTION

This disclosure is related to a surgical apparatus and associated methods in general for resecting and electrosurgically treating tissue. This disclosure is related more particularly to a system for use in arthroscopic surgery, including a powered hand-held instrument coupled to a mechanical resection blade integral with a plurality of electrodes for ablating, cutting or coagulating tissue.

BACKGROUND

Surgical tools designed for mechanical cutting of tissue have been used for a number of years. These types of tools typically include a powered handpiece and a rotating cutting blade, which is secured in the distal end of the handpiece. The blade may have an inner drive member including a hub drivingly engaged with an output shaft associated with a motor of the handpiece, and a drive shaft fixed to the hub, which defines a cutting implement, or head at a distal end thereof. An outer cannulated housing element is disposed about the drive shaft of the inner drive member and defines a cutting window thereon which cooperates with the moving cutting head to manipulate targeted patient tissue positioned adjacent the window.

Electrosurgical tools have also been available for many years, employing electrical energy to treat targeted patient tissue in various ways. For example, electrocauterization is utilized to seal off and close blood vessels during surgery to prevent blood loss. In addition, ablation may be utilized to vaporize or remove tissue using electrical energy. Electrosurgical probes are typically designed to perform both of these functions, depending upon the level of power supplied thereto. Further, monopolar and bipolar electrosurgical tools are conventional wherein monopolar tools direct electric current from an active electrode defined on the tool through the patient's body to a return electrode, the return electrode typically defined by a grounding pad attached to the patient. Bipolar tools, on the other hand, include both an active and return electrode, wherein the current is directed between the active electrode and the return electrode through the contacted tissue. More recent developments in electrosurgery employ a treatment device using Coblation® technology, developed by the assignee of the present invention. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. Upon sufficient energy being supplied to the vaporized conductive fluid, tissue may be volumetrically removed by molecular dissociation. A more detailed description of this phenomenon can be found in commonly assigned U.S. Pat. Nos. 5,697,882; 6,355,032; 6,149,120 and 6,296,136 the complete disclosure of which is incorporated herein by reference. More recently the assignee of the present invention has developed a further method of controlling the plasma field by regulating the volume flow rate of aspiration adjacent the active electrode, according to desired tissue effects and also in response to sensed parameters. This may improve control of the energy within the plasma and allow for more targeted tissue effect for a specific tissue type or procedure for example. A more detailed description of this phenomenon can be found in at least commonly assigned U.S. Pat. Nos. 8,192,424, 9,333,024 and 9,713,489 the complete disclosure of which is incorporated herein by reference.

In arthroscopic or endoscopic surgery both mechanical resection tools and electrosurgical tools are frequently interchanged within a single cannula, speaking to a need to combine both options in a single device. This may reduce surgery time and complication associated with blood loss. Combination devices generally tend to come with compromises. Firstly, the added functionality may require an increase in tip diameter or tip geometry, requiring larger and undesirable cannula sizes in the world of endoscopy and arthroscopy. A larger cannula size may also prevent access to required tissues. Alternatively, mechanical cutting surfaces may be recessed or reduced in size to allow space for the added functionality, but at a cost of potential reduced resection rates. Additionally the option to molecularly dissociate tissue as described above requires specific plasma resistant materials to be used, with added complexity when integrating in a mechanical resection device.

NOTATION AND NOMENCLATURE

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with a plasma.

"Mode of ablation" shall refer to one or more characteristics of an ablation. Lack of ablation (i.e., a lack of plasma) shall not be considered an "ablation mode." A mode which performs only coagulation shall not be considered an "ablation mode."

"Active electrode" shall mean an electrode of disclosed embodiments which produces an electrically-induced tissue-altering effect when brought into contact with, or close proximity to, a tissue targeted for treatment.

"Return electrode" shall mean an electrode of a disclosed embodiment which serves to provide a current flow path for electrical charges with respect to an active electrode, and/or an electrode of a disclosed embodiment which does not itself produce an electrically-induced tissue-altering effect on tissue targeted for treatment.

"Controlling flow of fluid" shall mean controlling a volume flow rate. Control of applied pressure to maintain a set point pressure (e.g., suction pressure) independent of volume flow rate of liquid caused by the applied pressure shall not be considered "controlling flow of fluid." However, varying applied pressure to maintain a set point volume flow rate of liquid shall be considered "controlling flow of fluid".

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

BRIEF DESCRIPTION OF THE DRAWINGS

For a detailed description of example embodiments, reference will now be made to the accompanying drawings in which:

FIGS. 4A and 4B are top and bottom exploded views of a blade distal tip, in accordance with the present disclosure;

SUMMARY

Figure 1:
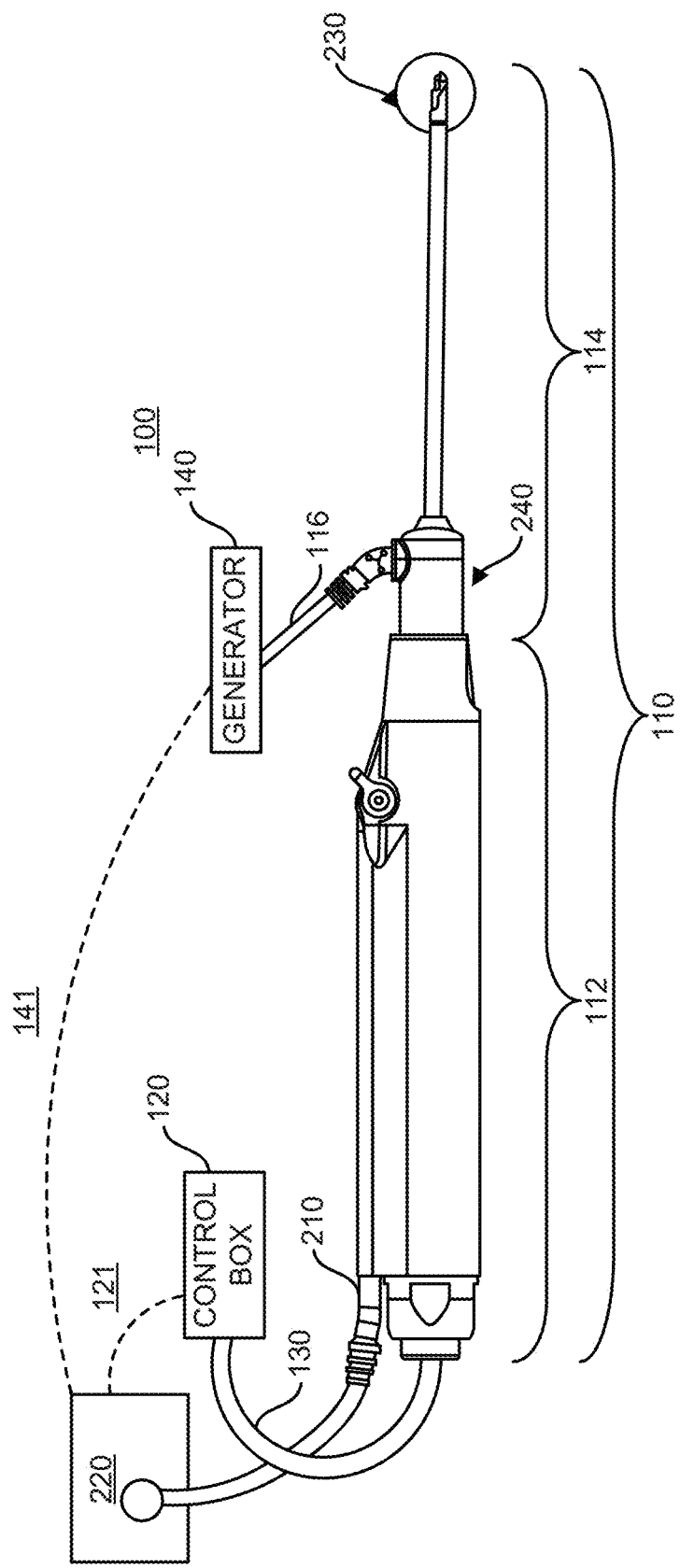
FIG. 1 schematically shows a system including a combination surgical device, and associated equipment connected to the surgical device, in accordance with the present disclosure.

Generally this disclosure describes a system including a combination device that both mechanically resects tissue and electrosurgically treats tissue. Various embodiments are therefore directed to a variety of systems and methods for removing tissue, using mechanical cutting, electrosurgical ablation and aspiration. The specification now turns to an example system.

Various embodiments are directed to a combination medical device for removing and treating tissue in a patient, including a handle portion and a blade portion. The handle portion includes a motor that is selectively able to be coupled to a control box for controlling the motor. The blade portion includes an outer sleeve with a lumen extending therethrough and an inner shaft along the lumen. The outer sleeve is fixed to the handle portion so as be a stationary sleeve. The outer sleeve has a window at the distal end, the window having a cutting edge. The inner shaft may also have a cutting edge at its distal end and is coupled to the motor, operable to cause the inner shaft to move and in cooperation with the outer sleeve window cutting edge mechanically cut tissue. The inner shaft may rotate for example. The outer sleeve comprises an electrically conductive material that is at least partially exposed defining an exposed electrically conductive portion at the distal end of outer sleeve. The outer sleeve also includes a lateral opening through the thickness of the outer sleeve wall, the lateral opening circumferentially spaced from the window. A dielectric spacer is coupled to the lateral opening, and extends through the lateral opening. The dielectric spacer may define a portion of the outer sleeve inner lumen. The spacer may have an inner surface that defines a portion of the outer sleeve lumen. The dielectric spacer may be configured to replace a portion of the outer sleeve and provide increased rigidity to the outer sleeve when compared to an outer sleeve with no latera opening. The dielectric spacer is configured to nest an active electrode and electrically isolates the active electrode from the outer sleeve. This allows the exposed electrically conductive portion to be electrically coupled to an RF generator and operate as a return electrode.

In some embodiments, the dielectric spacer may be ceramic, or a plasma-hardy dielectric material that is minimally degraded by adjacent plasma. The lateral opening may have a peripheral edge with a plurality of retention elements, such as axially spaced teeth elements that mesh with corresponding axially spaced retention elements on the dielectric spacer. The spacer may also have a circumferential overhang portion that partially wraps around/over an outer surface of the outer sleeve. The inner shaft may have a lumen that forms part of a fluid aspiration element, so as to remove tissue drawn through the window while mechanically resecting tissue and also so as to remove fluid and plasma by-products drawn through the active electrode while the device electrosurgically treats tissue. The active electrode may have an aspiration opening therethrough for delivering fluid and tissue debris into the inner shaft lumen.

Another embodiment device for removing and treating tissue in a patient may include an outer sleeve and a rotatable inner shaft disposed therein. The outer sleeve and inner shaft each have edge surfaces that mechanically cut tissue when the inner shaft rotates relative to the outer sleeve. The outer sleeve includes both an active electrode portion and a return electrode portion, electrically isolated from each other by a ceramic spacer. The ceramic spacer is spaced away from the outer sleeve edge surface and therefore does not form a portion of the mechanical cutting edge. The spacer extends through an opening in the outer sleeve from an outer circumferential surface of the outer sleeve towards an inner lumen surface of the outer sleeve.

This outer sleeve opening may having a peripheral edge with a plurality of retention elements, that mesh with complementary retention elements on the ceramic spacer so as to improve fixation of the ceramic to the metal outer sleeve. The plurality of retention elements may include a series of axially spaced teeth. The ceramic spacer may also include a circumferential overhang portion that partially wraps around an outer surface of the outer sleeve. This may improve fixation of the ceramic to the sleeve and also increase a distance between the active and return electrodes for improved electrosurgical tissue effect. The outer sleeve edge surface may form a portion of the return electrode. The inner shaft may also have a lumen that forms part of a fluid aspiration element, and therefore may remove tissue drawn through a window in the outer sleeve while the device mechanically resects tissue and also may remove fluid and plasma by-products drawn through the active electrode while the device electrosurgically treats tissue.

A further embodiment disclosed herein includes a system for mechanically resecting tissue and electrosurgically treating tissue. The system includes a motor drive unit and a blade that may be detachable to the motor drive unit. The motor drive unit and blade may each form a portion of a fluid aspiration conduit that is in fluid communication with each other. The system also includes a motor drive unit controller in communication with the motor drive unit, a fluid aspiration controller to control a flow rate through the motor drive unit and blade fluid aspiration conduits and an RF generator in electrical communication with an active and return electrode of the blade. The blade has an outer sleeve with an inner sleeve concentrically disposed therein, the inner sleeve coupled to the motor drive unit so as to the drive the inner sleeve and move it, relative to a stationary outer sleeve to mechanically cut tissue. The outer sleeve has an exposed electrically conductive portion coupled to the RF generator, sized so as to act as the return electrode. The outer sleeve also includes a ceramic spacer that extends through a lateral opening in the outer sleeve and replaces a portion of the outer sleeve, the ceramic spacer coupled to and electrically isolating an active electrode from the outer sleeve.

The fluid aspiration controller may be communicably coupled to the motor drive unit controller and also the RF generator so as to control a flow rate at a first flow rate when the motor drive unit controller is in operation and a second flow rate, different to the first flow rate when the RF generator is in operation. This second flow rate may be a variable flow rate, adjusted in response to a sensed parameter associated with an electrode circuit impedance of the blade.

A further embodiment disclosed herein may include a combination medical device for removing and treating tissue in a patient with a reusable handle portion and a blade portion selectively connectable to the handle portion. The blade portion includes an outer sleeve having a lumen with an inner shaft disposed therein, the inner sleeve coupled to a motor drive unit disposed within the handle portion. The inner sleeve is coupled to rotate and mechanically cut tissue. The outer sleeve may include at least one electrode for electrosurgically treating tissue. The reusable handle portion includes at least one control switch in electrical communication with the motor drive unit for controlling a parameter associated with the rotation of the inner shaft. The blade portion may also include a switch assembly in electrical communication with the at least one electrode, the switch assembly extending from a proximal end of the blade portion. The switch assembly may be selectively coupled to the reusable handle using attachment means. The switch assembly may include or be formed of a flexible substrate having first and second opposing sides, with attachment means on a first side and at least one button on the second side of the flexible substrate, and an electrically conductive element operably connected to the button for selectively coupling the at least one electrode with an output of an electrosurgical generator. The switch assembly attachment means may include an adhesive, or a clip, or a sleeve, or a wrap. The button may be a series of buttons or controls and may be operable to electrically couple two electrical contacts such that upon closure of the button the electrosurgical generator delivers energy to the at least one electrode. The button may be a series of buttons or controls and may be operable to electrically couple two electrical contacts such that upon closure of the button a fluid control apparatus adjusts the flow of fluid along the blade portion lumen and also controls the delivery of energy to the at least one electrode. The switch assembly may include two buttons, for selecting between two tissue treatment modes, each tissue treatment mode including a combination of energy delivery and fluid flow rate of fluid along the lumen of the blade portion.

A further embodiment disclosed herein may include a system for mechanically resecting tissue and electrosurgically treating tissue. The system may include a motor drive unit and a blade selectively coupled thereto, the motor drive unit and blade each having a fluid aspiration conduit in fluid communication with each other. The system may also include a motor drive unit controller communicably coupled to the motor drive unit and a fluid aspiration controller configured to control a flow rate through the motor drive unit and blade fluid aspiration conduits. The system may also include an RF generator in electrical communication with an active and return electrode of the blade. The blade may include an outer sleeve with an inner sleeve concentrically disposed therein, the inner sleeve coupled to the motor drive unit and configured to move relative to the outer sleeve to mechanically cut tissue. The inner sleeve may rotate relative to the outer sleeve. The outer sleeve may have a return electrode and active electrode on an outer surface of the outer sleeve at the distal end of the blade. The blade may also include a switch assembly in electrical communication with the return and active electrode, the switch assembly extending from a proximal end of the blade and including attachment means for selective attachment of the switch assembly to an external surface of the motor drive unit. The switch assembly may be formed of a flexible substrate having first and second opposing sides, a button on the second side of the flexible substrate, and an electrically conductive element operably connected to said button and at least partially disposed within the substrate. The electrically conductive element may be a series of wires for selectively coupling the active and return electrode with an output of the electrosurgical generator. The blade may include a cable for electrically coupling the blade with the RF generator, and the button may be operatively coupled to the cable. The switch assembly attachment means may be either an adhesive on a portion of the switch assembly, a clip, a sleeve or a wrap. The button is operable to electrically couple two electrical contacts such that upon closure the RF generator delivers energy to the active and return electrode. The switch assembly may include two buttons, for selecting between two tissue treatment modes. The button is operable to electrically couple two electrical contacts such that upon closure an RF generator delivers energy to the active and return electrodes and also adjusts a flow rate through the motor drive unit and blade fluid aspiration conduits.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The disclosure may generally include a system that combines mechanical resection with electrosurgical tissue treatments in a single device, electrosurgical tissue treatment including but not limited to tissue ablation, cutting and coagulation. Combining these two modalities may reduce the need for multiple instruments during surgery, such as endoscopic or arthroscopic surgery. The mechanical blade edge surfaces of both the stationary member and rotating member preferably comprise a metal. The active and return electrodes are preferably both disposed on a stationary outer sleeve portion of the blade, for reliable and simpler electrical communication between the electrodes and energy source. The electrodes are also integrated with or form a portion of the outer sleeve portion so as to minimally alter the outer diameter of the blade.

An overview of the surgical system 100 is best seen in FIG. 1, and includes a combination device 110 having a motor drive unit ("MDU") 112 mechanically coupled to a blade 114. Combination device 110 may be configured and operate similar to commercially available metal shavers or burrs with high speed rotating inner shafts disposed within a stationary outer sleeve. Combination device 110 also includes a RF bipolar power cord 116 electrically and mechanically coupled to blade 114 for supplying RF power to blade 114. Surgical system 100 further includes a control box 120 for supplying power to MDU 112 through a power cord 130, and an RF generator 140 for supplying RF power to blade 114 through RF power cord 116.

Furthermore, device 110 includes an aspiration tube 210 extending along the MDU 112 which may couple to an aspiration control mechanism 220. Aspiration control mechanism 220 may control a fluid flow through tube 210, and may be suction pump or plurality of suction pumps (not shown), a peristaltic pump having a rotor or other devices to provide and control aspiration of tissue and fluid. As a further example, the aspiration control mechanism may include a pinch valve having a plurality of positions that pinch or release the aspiration tube or the control mechanism may include a means of altering a fluid conduit size (orifice) associated with the aspiration tube. Aspiration control 220 may be in communication (141) with a controller of the RF power supply 140, and may also be in communication 121 with the control box 120 discussed in more detail later. Control box 120, generator 140 and aspiration control 220 are represented as separate enclosures; however these may be combined into a single enclosure in some embodiments. In alternative embodiments, the control box 120 and generator 140 may each have their own dedicated aspiration control system, and associated tubing and fluid flow control means. In alternative embodiments, aspiration may be at least partially controlled by a control valve disposed on the MDU 112 that may selectively allow stronger aspiration and reduce it during use. In this embodiment, the aspiration control 220 may supply a constant aspiration flow rate and manually be alterated by the user, by depressing the valve for example to alter the aspiration rate.

Blade 114 includes a lumen that extends through blade 114 and communicates with aspiration tube 210 for aspiration at distal portion 230, such that fluid and debris may be aspirated through a window in distal portion 230, flowing along lumen and through tube 210. Blade 114 includes a distal portion 230 that is inserted into a patient's body to cut tissue mechanically and to electrosurgically treat tissue. Blade 114 includes a proximal portion 240 configured to selectively connect and detach blade 114 to MDU 112, and configured to mechanically engage portions of blade 114 to a motor within the MDU 112.

Control box 120 may be, for example, the Dyonics® Power Shaver system or the Dyonics® EP-18 Shaver System supplied by Smith & Nephew, Inc. of Andover, Mass. Generator 140 may be a commercially available generator such as, for example, a COBLATION WEREWOLF system supplied by Smith and Nephew, Inc of Andover, Mass. The blade 114 is sized to accommodate the desired application. For example, for use in a shoulder the blade is sized differently from one for use in a prostate. Applications include, for example, use in a shoulder, a knee, and other joints, as well as use in natural orifices such as, for example, a uterus, a urethra, a nasal cavity, and a mouth.

Figure 2:
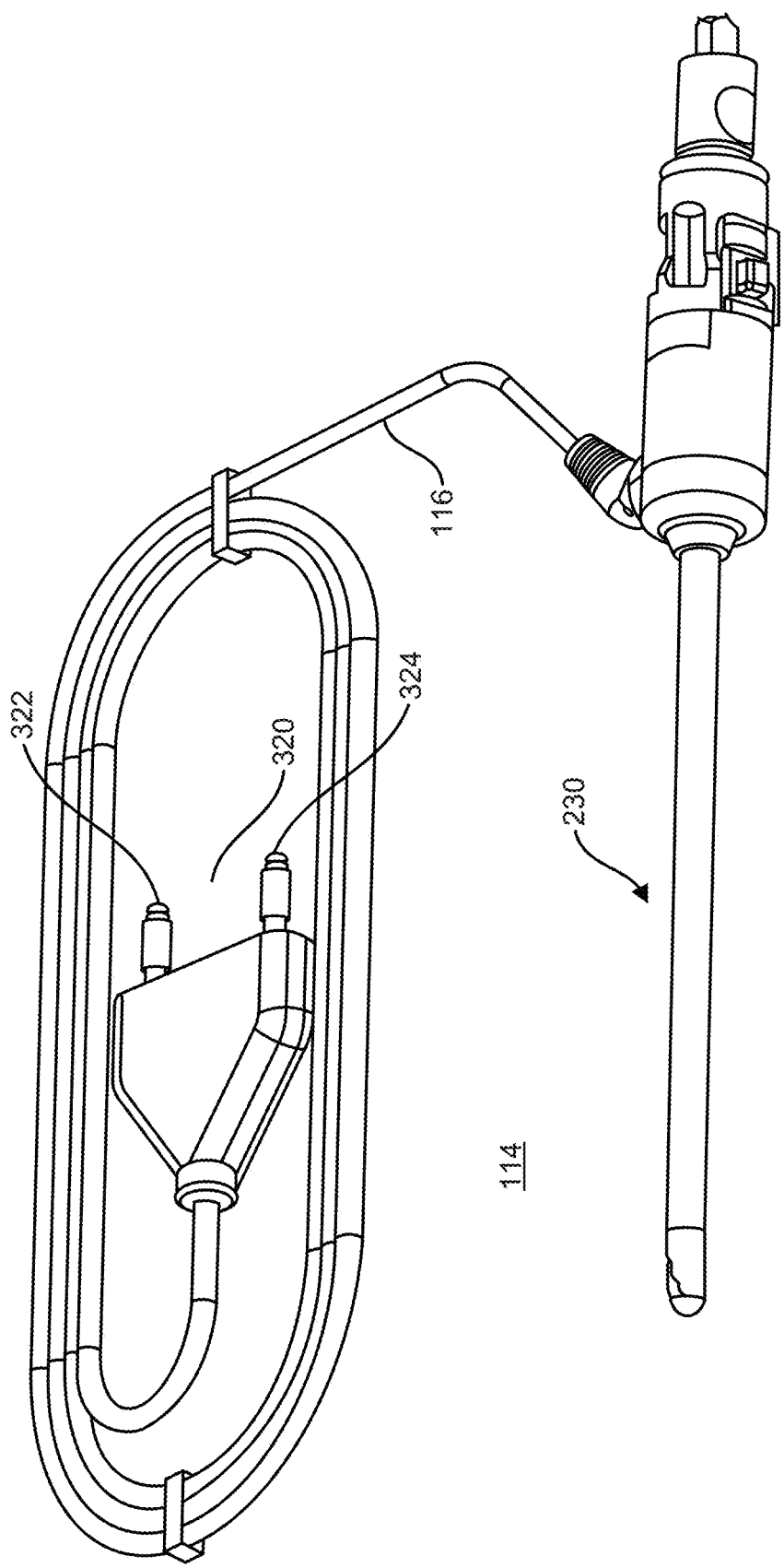
FIG. 2 schematically shows a blade portion of a combination surgical device, in accordance with the present disclosure.

Referring to FIG. 2, RF power cord 116 may terminate at a free end with a connector 320. Connector 320 may have at least two prongs 322 and 324 designed to connect to either a generator 140 or a foot switch. Each prong connects to one of two separate conductors within RF power cord 116 to provide both a supply path and a return path for blade 114. Additional prongs (not shown) may provide further information to the RF generator/controller 140 such as the type of device and/or desired or candidate settings such as fluid flow settings or power settings. Alternatively connector may include a series of pins configured to connect to a connector of an RF Controller 140, such as the system described in the commonly assigned U.S. Pat. No. 9,333,024 the complete disclosure of which is incorporated herein by reference.

MDU 112 includes a drive shaft (not shown) that is configured to selectively couple with a proximal end of blade 114, and may include coupling means similar to those disclosed in commonly assigned U.S. Pat. No. 7,150,747 the complete disclosure of which is incorporated herein by reference.

Aspiration controller 220 may be in communication with both the MDU control box 120 and RF generator 140, represented in FIG. 1, such that during times that the MDU is in operation, aspiration rates may be controlled at a fluid flow rate regulated by the control box 120. This may further be dynamically altered in response to sensed parameters associated with the MDU or sensed temperature in a patient's joint. Furthermore, during times that the RF Generator 140 is in operation, aspiration may be controlled at a fluid flow rate commanded by the RF generator 140. The fluid flow rate may further dynamically altered in response to sensed parameters such as electrode circuit impedance as described in commonly assigned U.S. Pat. Nos. 8,192,424 and 9,333,024 the complete disclosure of which is incorporated herein by reference.

Generally the blade 114 mechanically resects in a manner similar to other commercially available mechanical resections devices; in that blade 114 includes an outer sleeve 310 that is fixedly attached to the MDU 112 and is a stationary sleeve during use, and an inner sleeve 410, concentric with the outer sleeve, coupled to the MDU 112 such that it may rotate at high speeds relative to the stationary outer sleeve 310. Blade 114 can be attached to MDU 112 using various structures, for example, threaded connections and pressure-fit connections. Various embodiments of MDU 112 include motor drive units manufactured by Smith & Nephew, Inc., of Andover, Mass., such as, for example, part numbers 7205354, 7205355, and 7205971.

A variety of cutting surfaces can provide mechanical cutting. Such surfaces include, for example, blades that are curved, burred, straight, serrated, or miniature. Mechanical cutting is typically achieved with speeds in the thousands of cycles (for example, revolutions or reciprocations) per minute.

Now referring to FIGS. 3A-3D showing an embodiment of the blade distal tip 340, outer sleeve 310 includes a longitudinal opening 320 defining an edge surface 325 around at least a portion of the perimeter of the opening 320. Edge surface 325 is preferably sufficiently sharp to cut tissue when used in combination with the inner sleeve 410. Inner sleeve 410 may have a similar opening 420 and edge surface 425 that is configured to cooperate with edge surface 325 to mechanically resect tissue as the inner sleeve rotates. Inner sleeve 410 and opening 420 may be in communication with aspiration tube 210 such that inner sleeve 410 defines an elongate fluid conduit along its lumen (not shown) so that tissue debris formed during mechanical resection may be removed through said conduit and opening 420. Both inner and outer sleeves (410 and 310) including their cutting edge surfaces 425 and 325 may be formed from a metal such as stainless steel as the inventors have found this material offers good strength generally and a durable cutting edge. An alternative option for one of the sleeves may be Invar, a nickel-iron alloy that is readily brazed to. A metal cutting edge is preferable to reduce particulate formation during cutting, which can occur with more brittle materials.

Outer sleeve 310 is preferably a metallic or electrically conductive tube, configured to provide an electrical path from the electrical cord 116 to blade distal tip. Outer sleeve 310 may be at least partially coated or covered by a layer or sheath 305 to electrically insulate a portion of the outer sleeve 310 and limit an exposed portion of the outer sleeve to controlled areas. For example a proximal portion of the outer sleeve 310, adjacent the MDU 112 may be exposed sufficient to electrically couple with cord 116 and thereby the RF generator 140 (not shown). A distal portion of the outer sleeve 310 may also be left exposed, so that the metallic cutting edge surface 325 is exposed for mechanical resection and also such that a surface area is exposed defining the return electrode 350 of the system 100, for use during application of the RF energy.

Outer sleeve 310 further comprises an active electrode 360, electrically coupled to the RF generator 140 via cables or wires (not shown) and electrically insulated from the outer sleeve 310 and thereby return electrode 350 via an electrically insulative spacer 370. Since the active electrode 360 is intended to selectively ablate tissue and therefore form plasma, spacer 370 is preferably an electrically insulative material that is also resistant to degradation from plasma, or plasma-hardy. Materials may include a ceramic or glass material, such as alumina, zirconia and the like. The preferred embodiment may use a unique high strength and fracture-resistant ceramic such as zirconia. This ceramic is capable of being molded into detailed shapes similar to alumina, but it will not decompose under plasma like traditional zirconia. Silicon Nitride is a further option.

In addition, the active electrode 360 should preferably be a material that is resistant to degradation to plasma, such as a tungsten, titanium, platinum, molybdenum, aluminum, gold and copper. More specifically the active electrode may preferably be a different material from the inner and outer sleeve material. While stainless steel is preferred for the mechanical cutting edges, stainless steel tends to be less resistant to degradation by plasma and therefore is not the preferred material for an ablation electrode. In addition, tungsten for example is a more brittle metal than stainless steel and therefore would not be preferable as a cutting edge, as particulate may form during mechanical resection. Additionally the inventors have found that the portion of the distal end that forms plasma should be spaced away from the mechanical cutting edge, as whatever the material of choice for the mechanical cutting edge, the edge may be degraded by the plasma and mechanical cutting may be compromised. Asperities such as sharp edges have more tendancy to form plasma thereon, therefore a minimum distance between peripheral edges of the active electrode 360 and the cutting edge 325 should be at least 2 mm. The portion of the distal end that forms plasma should be spaced away from the mechanical cutting edge, such that plasma formation along the mechanical cutting edge is not preferential.

In order to maintain a smaller outer diameter of the distal tip 340, spacer 370 may replace a portion of the outer sleeve 310 so as to extend through the wall thickness of outer sleeve 310 from the outer surface towards the inner lumen. Stated otherwise outer sleeve 310 comprises a second opening 330, for receiving a spacer 370 therethrough. Opening 330 may be an enclosed opening, spaced away from the cutting edge 325 and distal-most tip of the outer sleeve 310 and may be at least partially diametrically opposite opening 320. Opening 330 preferably axially overlaps opening 420 of inner sleeve. Spacer 370 is preferably formed from a high-strength ceramic which provides structural integrity to the outer sleeve 310, and may add rigidity to the outer sleeve so as to provide a strength improvement compared to an all metal outer sleeve. Insulative spacer 370 is not used as a cutting surface, but instead serves to seal off the metal inner sleeve 410 and provide insulation from the plasma. Spacer 370 extends through the second opening 330 but preferably does not extend into or intrude into the outer sleeve lumen, as this may interfere with the inner sleeve 410 as it rotates. Best seen in FIG. 3C spacer 370 may extend through second opening 330 up to the inner lumen wall 312 of outer sleeve 310. Inner curved surface 371 of spacer 370 may be curved so as be substantially continuous with the curvature of inner lumen wall 312. Compared to a spacer that may solely lie on an outer surface of the outer sleeve 310, replacing a portion of the outer sleeve 310 with spacer 370 allows for a significantly smaller overall cross-section to be maintained (See FIG. 3C), while still maintaining spacing requirements between active and return electrodes to control the electrical path between the two electrodes. Thus with the spacer configuration as disclosed, minimal increase to outer cross section of device is achieved. For example, the inventors have found that if outer sleeve outer diameter (OD) is approximately 4.5 mm, similar to existing devices such as the Platinum Bonecutter, the maximum cross-section (CS) including spacer 370 and electrode 360 still fits through a 5 mm cannula.

Further detail of the spacer 370 and active electrode 360 are best seen in FIGS. 4A and 4B, showing exploded views of the top side and underside of distal portion 340. Second opening 330 extends through to inner lumen of outer sleeve 310 and inner sleeve 410 may be seen therethrough in FIGS. 4A and 4B. Inner sleeve 410 may be preferably oriented such that inner sleeve opening 420 is in fluid communication with second opening 330 during operation of the RF generator 140. Stated otherwise inner sleeve opening 420 may preferably be facing second opening 330 during operation of ablation mode. (Figures show inner sleeve opening 420 facing away from opening 330). In some modes this inner sleeve opening 420 may be rotated so as to only partially overlap second opening 330 or adjustably overlap second opening 330, as a means of controlling the fluid flow rate through the active electrode 360, spacer 370 and second opening 330. This may further control the tissue effect and energy within any plasma formed at the active electrode 360, as explained earlier. Alternatively, the inner sleeve opening 420 may be aligned with second opening 330 and the volume flow rate may be controlled using a flow control device such as a pump in communication with controller 220.

Figure 3A:
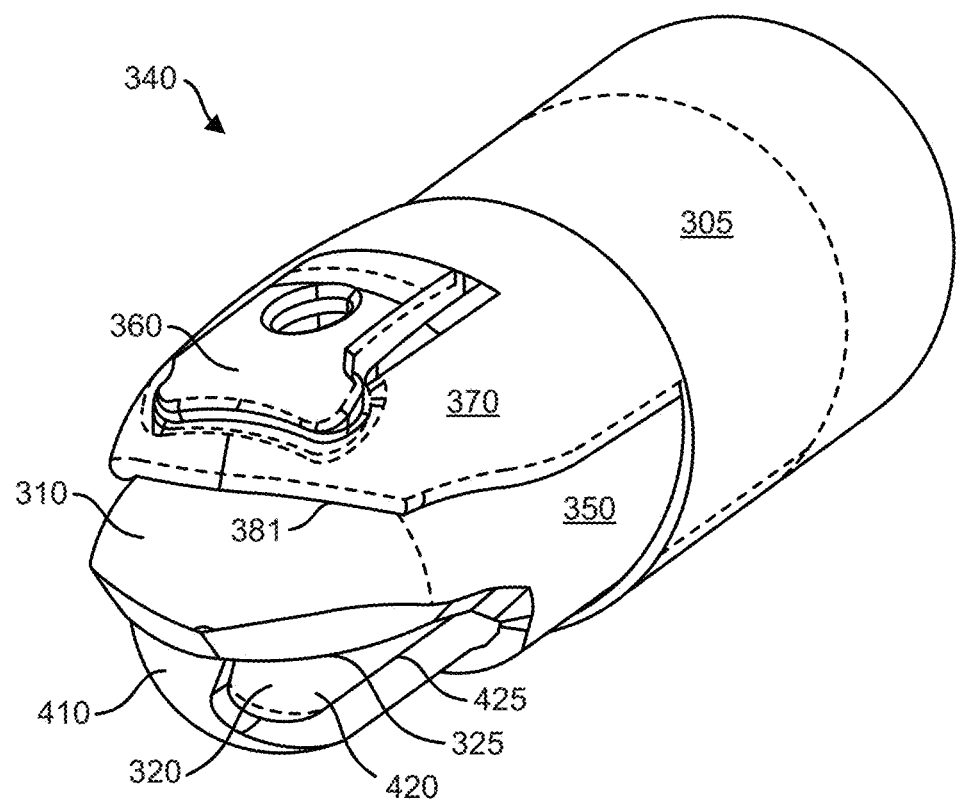
FIG. 3A is a isometric view of a blade distal portion of a combination surgical device, in accordance with the present disclosure.
Figure 3B:
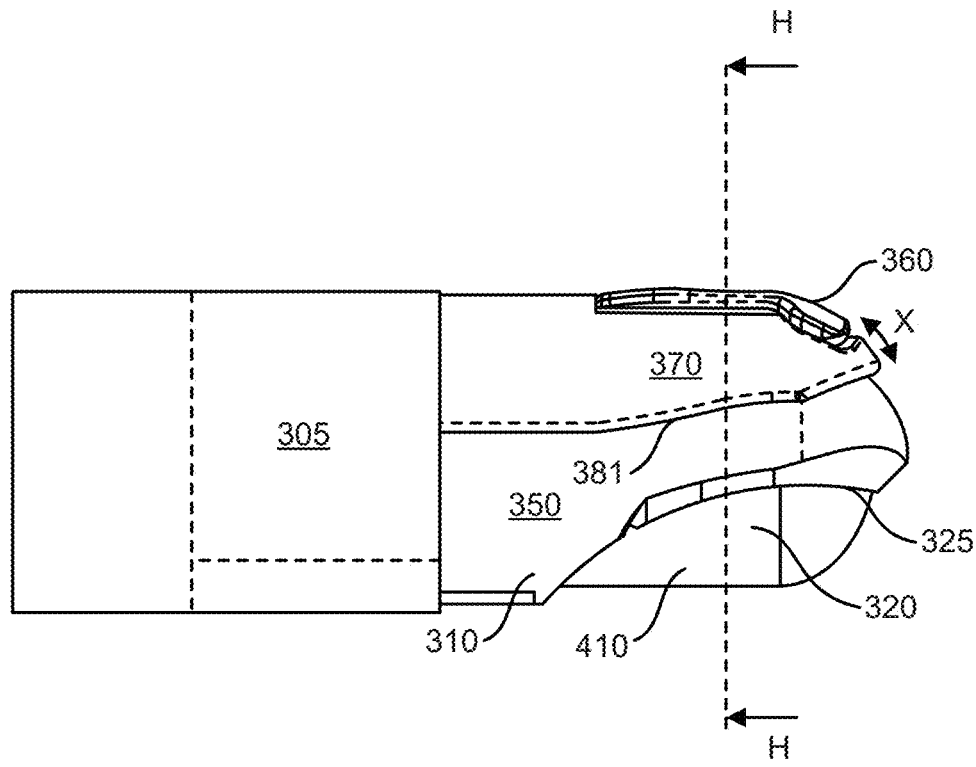
FIG. 3B is a side view of a blade distal portion, in accordance with the present disclosure.
Figure 3C:
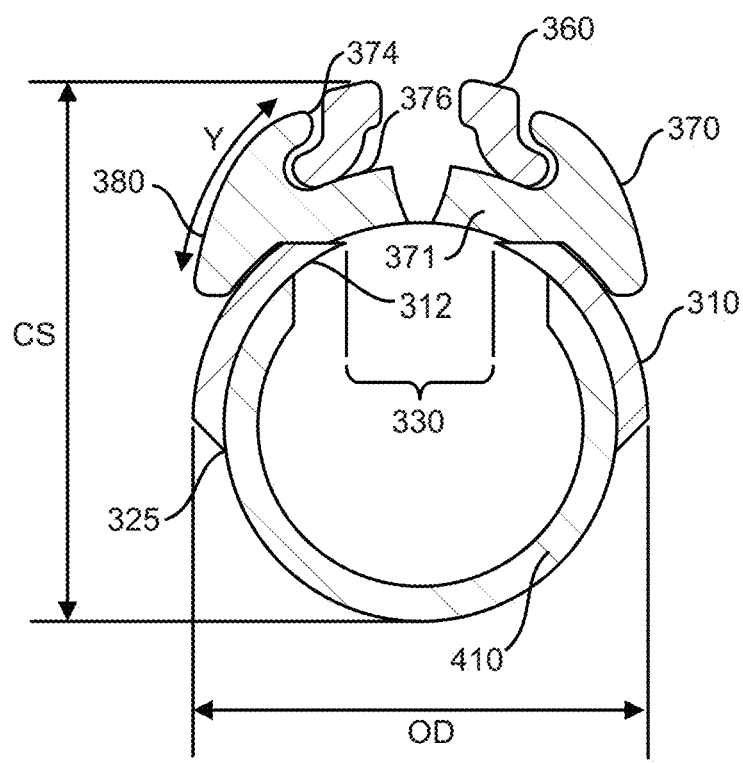
FIG. 3C is a perpendicular cross-section of a blade distal tip, in accordance with the present disclosure.
Figure 3D:
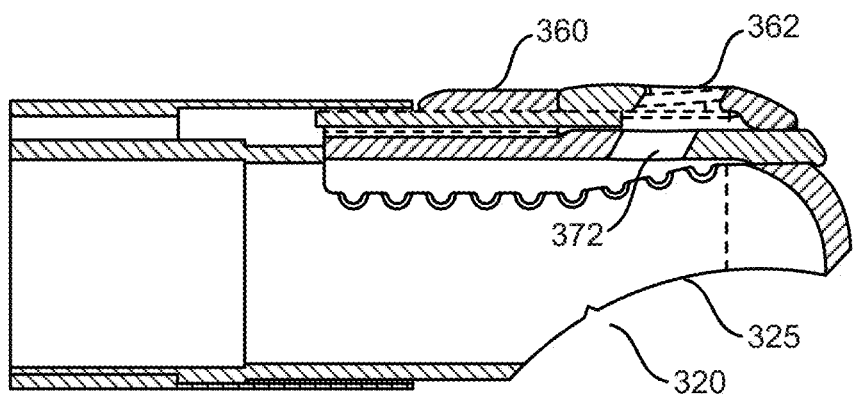
FIG. 3D is a longitudinal cross-section of a blade distal tip, in accordance with the present disclosure.

Second opening 330 may include mechanical locking features 335, such as a plurality of axially spaced teeth to better couple the spacer 370 with outer sleeve 310. Complementary retention features 375 may be seen on spacer 370 in FIG. 4B, the teeth formation configured to improve stresses distribution between the two parts. Bond strength may also be improved due to the increased contact area. Spacer retention features 375 may be recessed within the spacer 370 surrounding by overhang 380, seen in both FIGS. 4B and 3C. This overhang 380 provides several advantages. Firstly it better distributes stress between the spacer 370 and outer sleeve 310 due to any side loading during use of the device. It also increases surface area contact between the spacer 370 and outer sleeve 310 adding area for adhesive coupling. In addition, this overhang 380 provides a preferred electrical insulation gap between the return electrode 350 and active electrode 360, and thus improving plasma formation around the active electrode 360. Gap is shown in FIGS. 3B and 3C as spacing X and Y. Too small a distance between the two electrodes can disrupt the high voltage build up that form plasma, and electrical shorting may occur. Additionally the profile or peripheral edge 381 of the overhang follows the peripheral edge surface profile of the cutting window 325 to maintain visibility of the window 325, and limit visibility being obscured by the ceramic spacer 370.

Spacer 370 includes aspiration opening 372 through the thickness of spacer 370 so as to be in fluid communication with inner lumen of outer sleeve 310. As discussed earlier, when inner sleeve opening 420 is oriented so as to at least partially face or be in fluid communication with aspiration opening 372, aspiration of fluid and plasma and coagulation by-products may be removed from the tissue treatment site, allowing the same aspiration path to be used for both mechanical resection and RF tissue treatment. Typically, this would require the active electrode 360 to be offset farther from the return 350 to prevent plasma from forming inside the device. (The distance between the active and return on the inside of the device must preferably be greater than the distance between the active and return at the outer surface of the device). Since a portion of the inside of the outer sleeve 310 is now replaced with insulative spacer 370 (curved surface portion 371) the distance from the active electrode 360 to return 350 (surface 312) is now increased, thereby minimizing unintended plasma inside the device. Active electrode 360 also includes at least one aspiration opening 362 in fluid communication with aspiration opening 372 of the spacer 370, to remove debris and plasma by-products through the active electrode surface during use. Active electrode 360 has a rounded outer surface and nests within a spacer cavity 376, minimizing any additional size increase so the device may fit within a 5 mm cannula. The active electrode 360 is constrained and supported by the ceramic spacer 370, by a slot 373 and bilateral overhangs 374 on lateral sides of cavity 376. Electrode flange or tail 363 slides into slot 373 in the spacer 370 and lateral portions of the electrode 360 are partially covered by overhangs 374. Overhangs 374 further increases distance between active electrode 360 and return electrode 350. This type of mechanical interface is possible by using a metal-injection moulded electrode 360, ideally composed of predominantly tungsten. Flange 363 is electrically conductive and forms a portion of the electrical path from active electrode 360 to RF generator. Flange 363 may be a moulded portion of the electrode 360 so that the flange 363 and electrode 360 are a single moulded piece. Alternatively, flange 363 may be an electrically conductive wire or cable, electrically coupled to the electrode 360. Electrically conductive cable or flexible circuit (not shown) may be electrically coupled to the flange 363 or electrode 360 and extend along outer sleeve 310 to a proximal portion of blade 114 and electrical cord 116. This electrically conductive cable is electrically isolated from outer sleeve 310, as outer sleeve 310 preferably provides the electrically conductive path for the return electrode 350 to the cord 116.

Active electrode 360 may have a concave underside 364. This is to increase distance between the active electrode 360 and inner sleeve 410, and mitigate the inner sleeve 410 inadvertently acting as an electrical path shunt in some orientations and thereby effecting plasma formation. This may occur if the active electrode is not concave or is too close to the metallic inner sleeve 410. As discussed earlier, in order for consistent plasma to be formed on the outer portion of the active electrode 360, the spacing between the internal surfaces of the active and return electrodes should preferably be further than the distances X and Y on outer surface portions. While the outer sleeve 310 is coupled as the return electrode, there may be no electrically insulative means between the inner and outer sleeve (410 and 310 respectively). Given that the inner sleeve may be in contact with the outer sleeve is some locations, the inner sleeve 410 is at times electrically coupled to the outer sleeve and thereby may form part of the return path. Therefore it is to be assumed that the inner sleeve 410 may be operable to form a portion of the electrically conductive path as it contacts the inner lumen of the outer sleeve 310. It follows therefore that the inner sleeve 410 may bridge or shunt the electrical path between the active electrode inner surface 364 and return electrode 350, when the inner sleeve is in certain orientations, such as the orientation shown in FIG. 4A. If inner sleeve 410 is rotated as shown in FIGS. 4A and 4B, the spacing between the inner surface 364 and an outer surface of the inner sleeve 310 should preferably by further than the distance X and/or Y as described in FIGS. 3B and 3C. A concave inner surface 364 is one means of achieving this minimum spacing. An alternative means includes a boss, described in later figures.

Active electrode has a distal tip 368 that may extend around the rounded distal tip of outer sleeve, to minimize device cross-section and also provide for an RF tissue effect at the distal-most tip of the device. Distal tip 368 may also be tapered to minimize the overall diameter at the tip for improved access to tight areas. The outer curved surface, together with the recessed position of the active electrode 360 within spacer 370 also minimizes tissue snagging with manipulating the device. In addition to reducing snagging, the blade distal end should include components that transition smoothly with each other, and preferably have a curved and smooth outer profile. This maintains the feel or tactile feedback of the device similar to devices that the surgeon is familiar with such as pure mechanical resection devices only. The tactile feedback is important to the feel of the device while mechanically resecting or generally manipulating tissue.

Aspiration through the active electrode 360 and spacer 370 may be controlled by a "Window Lock" feature of the shaver. The surgeon has the capability to set the opening 420 of the inner sleeve 410 to "closed", thereby allowing flow exclusively through opening 362 through the active electrode 360. This may be necessary to clear the field of bubbles created during the RF plasma ablation. Laser marks may be added to the inner and/or outer sleeve to show alignment when the opening 420 is closed. By sharing the aspiration channel with the mechanical resection handle, the surgeon can also customize ablation performance by controlling aspiration on the handle. Seen best in FIG. 3D aspiration openings 362 and 372 may be angled and slightly axially offset from each other. This may help direct flow or debris and by-products proximally.

Figure 5A:
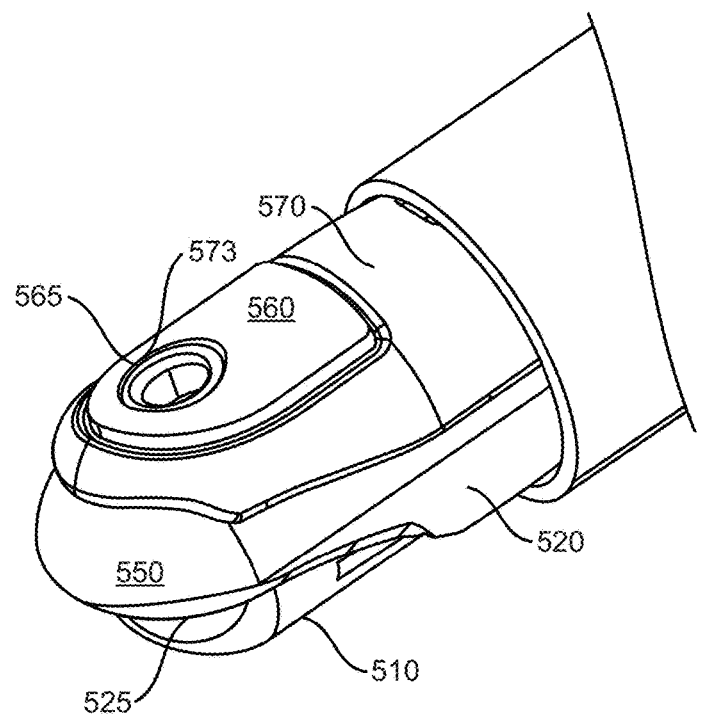
FIGS. 5A, 5B and 5C show a plurality of views of an alternative embodiment of a blade distal tip, in accordance with the present disclosure.

FIG. 5A shows an isometric view of an alternative embodiment for a blade distal portion. Similar to the previously described embodiment, blade distal portion includes an inner sleeve 510, outer sleeve 520, active electrode 560 and spacer 570. Outer sleeve 520 and inner sleeve 510 may both have openings with sharp edges to mechanically cut tissue. Active electrode 560 may be electrically coupled to the RF generator 140 via cables or wires and electrically insulated from the outer sleeve 520 and thereby return electrode 550 via an electrically insulative spacer 570. Similar material factors such as plasma hardiness and durable cutting surfaces as described for previously embodiments are considered for the spacer, outer sleeve and active electrode 560.

Figures 5B, 5C:
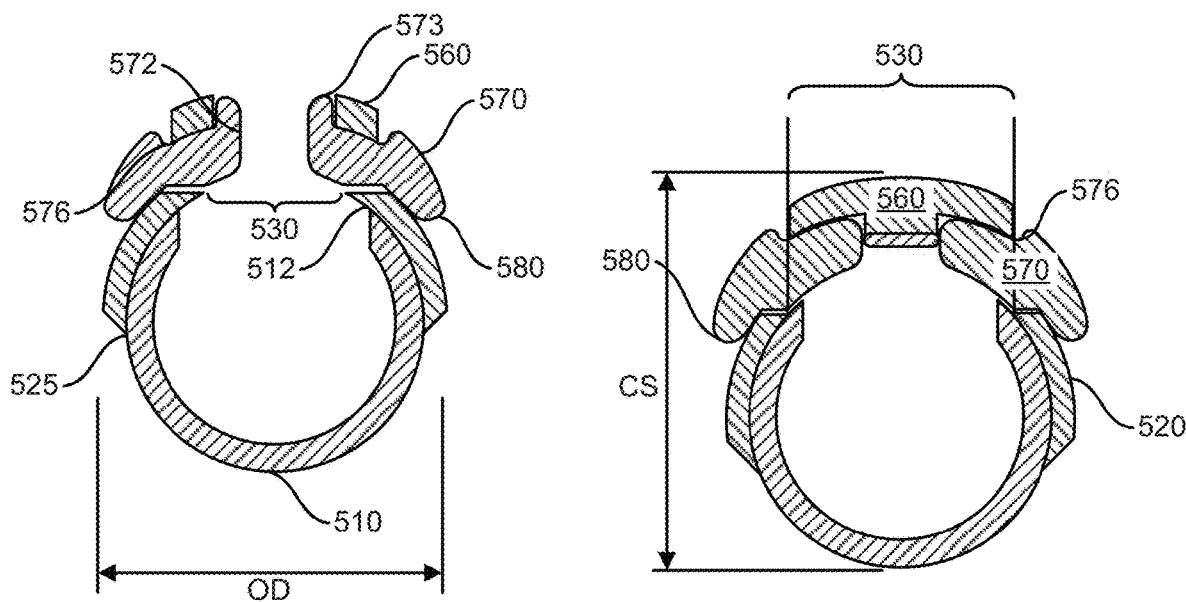

In order to maintain a smaller outer diameter of the distal portion, spacer 570 may replace a portion of the outer sleeve 560 so as to extend through the wall thickness of outer sleeve 560 from the outer surface towards or up to the inner lumen. Opening 530 may be an enclosed opening, spaced away from the cutting edge 525 and distal-most tip of the outer sleeve 520. Spacer 570 is preferably formed from a high-strength ceramic which provides structural integrity to the outer sleeve 520, and may add rigidity to the outer sleeve 520 so as to provide a strength improvement. Insulative spacer 570 is not preferably used as a cutting surface, but instead serves to seal off the metal inner sleeve 510 and provide insulation for the RF ablation plasma. Spacer 570 extends through the opening 530 but preferably does not extend into or intrude into the outer sleeve lumen, as this may interfere with the inner sleeve 510 as it rotates. Best seen in FIGS. 5B and 5C showing cross sections of FIG. 5A, spacer 570 may extend through opening 530 towards but not beyond the inner lumen wall of outer sleeve 520. Inner curved surface of spacer 570 may be curved so as be substantially continuous with the curvature of inner lumen wall 512. By making this hybrid tip, with the spacer 570 replacing a portion of the outer sleeve 520 a significantly smaller overall cross-section is maintained (See FIGS. 5B and 5C). Thus with the spacer configuration as disclosed, minimal increase to outer cross section of device is necessary. For example, the inventors have found that if outer sleeve outer diameter (OD) is approximately 4.5 mm, similar to existing devices such as the Platinum Bonecutter, the maximum cross-section (CS) including spacer 570 and electrode 560 still fits through a 5 mm cannula.

Not shown in FIGS. 5A-5C, opening 530 and spacer 570 may include mechanical locking features similar to those described in FIGS. 4A and 4B. Spacer 570 may also include overhang 580, seen in both FIGS. 5B and 5C to improve stress distribution between the spacer 570 and outer sleeve 520 due to any side loading during use of the device. Overhang 580 may also increase surface area contact between the spacer 570 and outer sleeve 520 adding area for adhesive coupling. In addition, this overhang 580 provides a preferred gap between the return electrode 550 and active electrode 560, to form consistent plasma at the active electrode 560; gaps similar to those shown in FIGS. 3B and 3C as spacing X and Y.

Spacer 570 includes aspiration-opening 572 through the thickness of spacer 570 in fluid communication with inner lumen of outer sleeve 520. In this embodiment, the aspiration opening 572 includes a boss 573, to increase dielectric spacing between the active electrode 560 and effective return electrode. As explained previously it is preferable that the distance between the active and return on the inside of the device be greater than the distance between the active and return at the outer surface of the device. Since a portion of the inside of the outer sleeve 520 is now replaced with insulative spacer 570, adding the boss 573 at the opening 572 increases the distance from the active electrode 560 to return electrode 550, thereby minimizing unintended plasma formation inside the device. Boss 573 extends through and nests within a complimentary opening 565 in the active electrode 560, terminating to be slightly recessed from the top surface of active electrode 560. This maintains an exposed edge surface around the active electrode opening 565 to focus the electrical field and form plasma at the edges of opening 565. Aspiration opening 565 and boss 573 are sized to remove tissue debris and plasma by-products from the active electrode surface during use. Active electrode 560 has a rounded outer surface and nests a least partially within a spacer cavity 576 so as to keep the distal tip cross-section minimalized, and fit within a 5 mm cannula. Unlike the embodiment in previous figures, that disclosed a concaved underside of the active electrode, this embodiment of the active electrode 560 may be flush within the spacer cavity 576 as the boss 573 provides the supplemental electrical pathway spacing to preference the primary electrical pathway on the outer surface of the device. This may further reduce the distal tip cross section. This may also provide a better tactic feel as described earlier.

In addition to manual control, the device 110 may be connected directly to the WEREWOLF◊ COBLATION◊

System, owned by the common assignee of this application and incorporated herein by reference. This allows automated control of suction when COBLATION is active and may provide constant or controlled suction for the shaver device when COBLATION is not active. Shaver flow control can be controlled based on a variety of feedback such as pressure in the tubing, power draw the motor, torque transducer connected to the motor, and/or motor temperature. The flow control module can also be run in reverse to remove clogs.

This combination device 110 may also have a coagulation mode characterized generally as a lower voltage mode relative to ablation mode. The coagulation field of this device 110 is contained to the area around the active electrode 360. This controlled area reduces unintended thermal tissue damage.

The electrical path for this device may use a flex circuit on the outside of the outer sleeve 310 for power delivery to the active electrode. This same flex circuit may incorporate the circuit to enable Ambient◊ technology, owned by the common assignee of this application and incorporated herein by reference. Ambient technology provides temperature information to the RF Controller and/or the control box 120 thereby sensing a value indicative of temperature of fluid inside the joint during both mechanical resection and RF tissue treatment. A sensor for sensing a value indicative of temperature may be coupled to any portion of the device distal tip 340, and may for example by coupled to a portion of the spacer, axially spaced proximally from the active electrode.

Figure 6B:
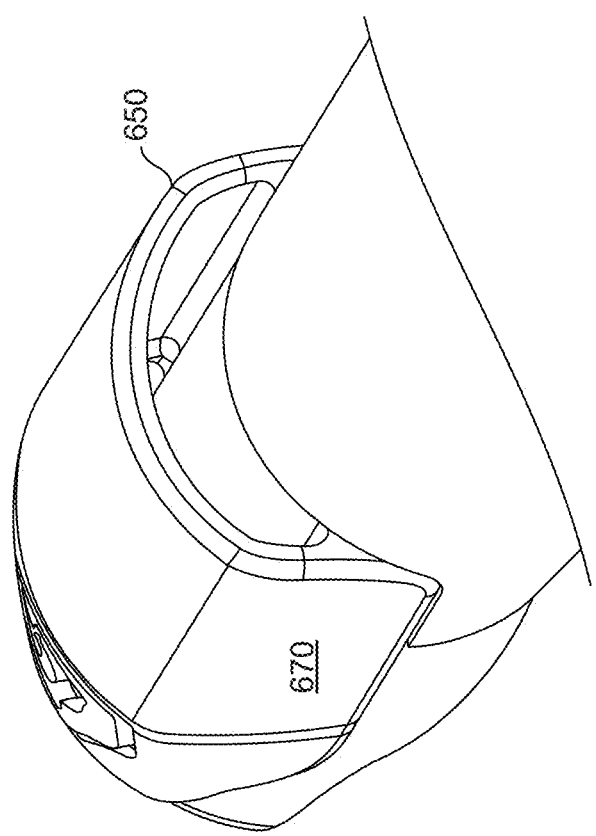
FIGS. 6A and 6B show two differing views of an alternative embodiment of a blade distal tip, in accordance with the present disclosure.
Figure 6A:
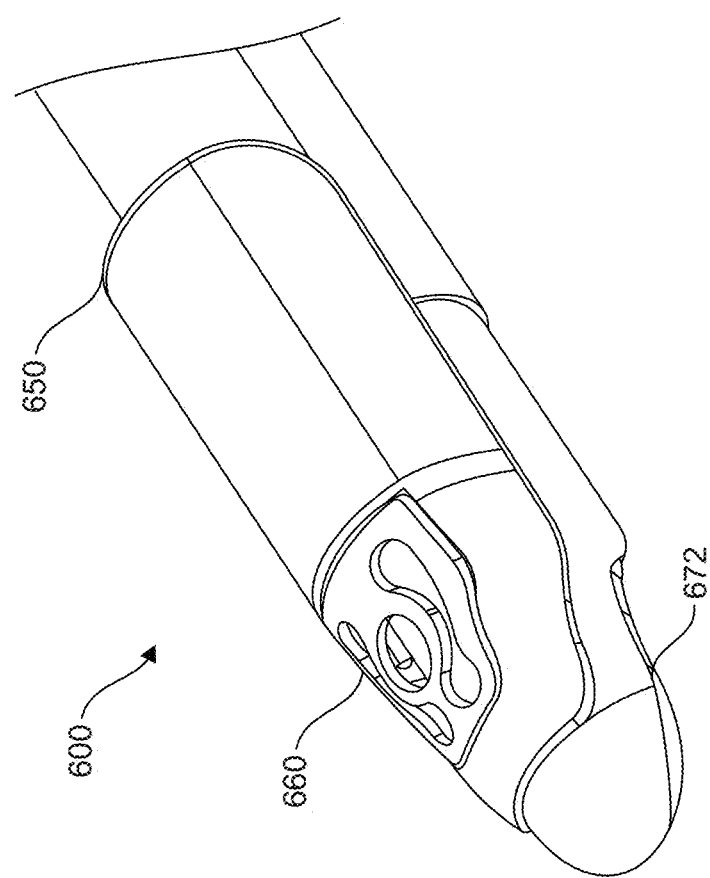

An alternative embodiment of a blade distal portion 600 is shown in FIGS. 6A and 6B which includes a dedicated suction channel 650 for operation while delivery RF energy to the blade distal portion 600. Features such as the cutting windows or openings and return electrode may be similar to the previously disclosed embodiments. Suction channel 650 may be a portion of spacer 670, which may extend proximally along device shaft. In this embodiment, a suction path separate from the mechanical resection aspiration path, extends along an outer portion of the device and connects with a separate suction tube (not shown) directly coupled to a flow control device associated with the RF control device only. This may allow a more customized aspiration profile and thereby a more customized ablation performance (such as with the Werewolf Flow Control module or similar method). Also of note, active electrode 660 may include a plurality of aspiration openings 672, each having a different shape.

Figure 7C:
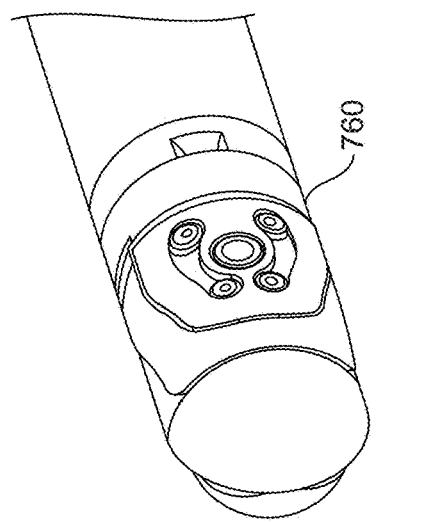
FIGS. 7A, 7B and 7C show a plurality of views of an alternative embodiment of a blade distal tip, in accordance with the present disclosure.
Figure 7B:
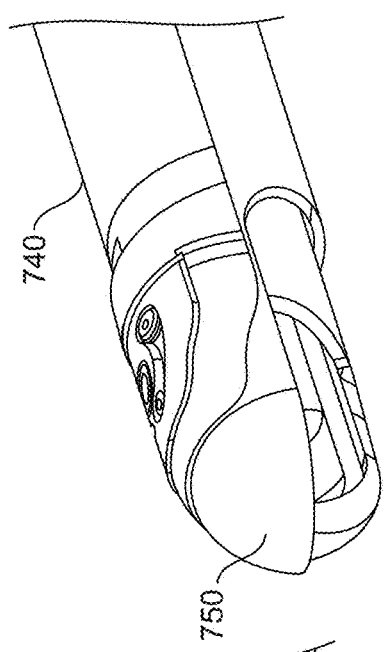
Figure 7A:
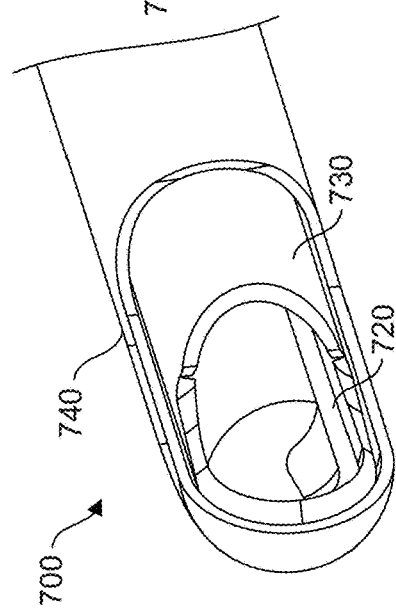

A further alternate embodiment of a blade distal portion 700 is shown from various angles in FIGS. 7A, 7B and 7C. Features such as the cutting windows or openings and return electrode may be similar to the previously disclosed embodiments. This embodiment includes a shield or middle tube 730, in addition to inner tube 720 and outer tube 750. Similar to previous embodiments, active electrode 760 is supported by spacer 740 coupled to outer tube 750, which may provide the return path of the RF output. This device is similar to the "Orbit"-style shavers. The shield of middle tube 730 can be used to control suction, thereby preventing the need to set a "Window-Lock" to control suction. Shown in FIG. 7A, shield 730 is in an open configuration and inner tube 720 may rotate relative to shield 730 to mechanically resect tissue and aspirate the tissue debris through a lumen of inner tube. In this open configuration, there may be no aspiration available to the active electrode 760, should energy be supplied, which may be preferable for some tissue treatments. Of note edges along the respectively openings of middle tube 730 and inner tube, 720 provide the tissue resection. FIG. 7B shows the shield in a partial open configuration which may provide some aspiration through active electrode 760 and also through the inner tube lumen. In this partially open configuration, mechanical resection and electrosurgical tissue treatment may be used in combination or sequentially. This configuration may also be configured so control a rate of aspiration. In a third and closed configuration, shield 730 may be rotated to completely cover inner tube 720 and have an opening facing an underside of active electrode 760. Aspiration may be provided to the apertures predominantly through the active electrode 760.

Figure 8:
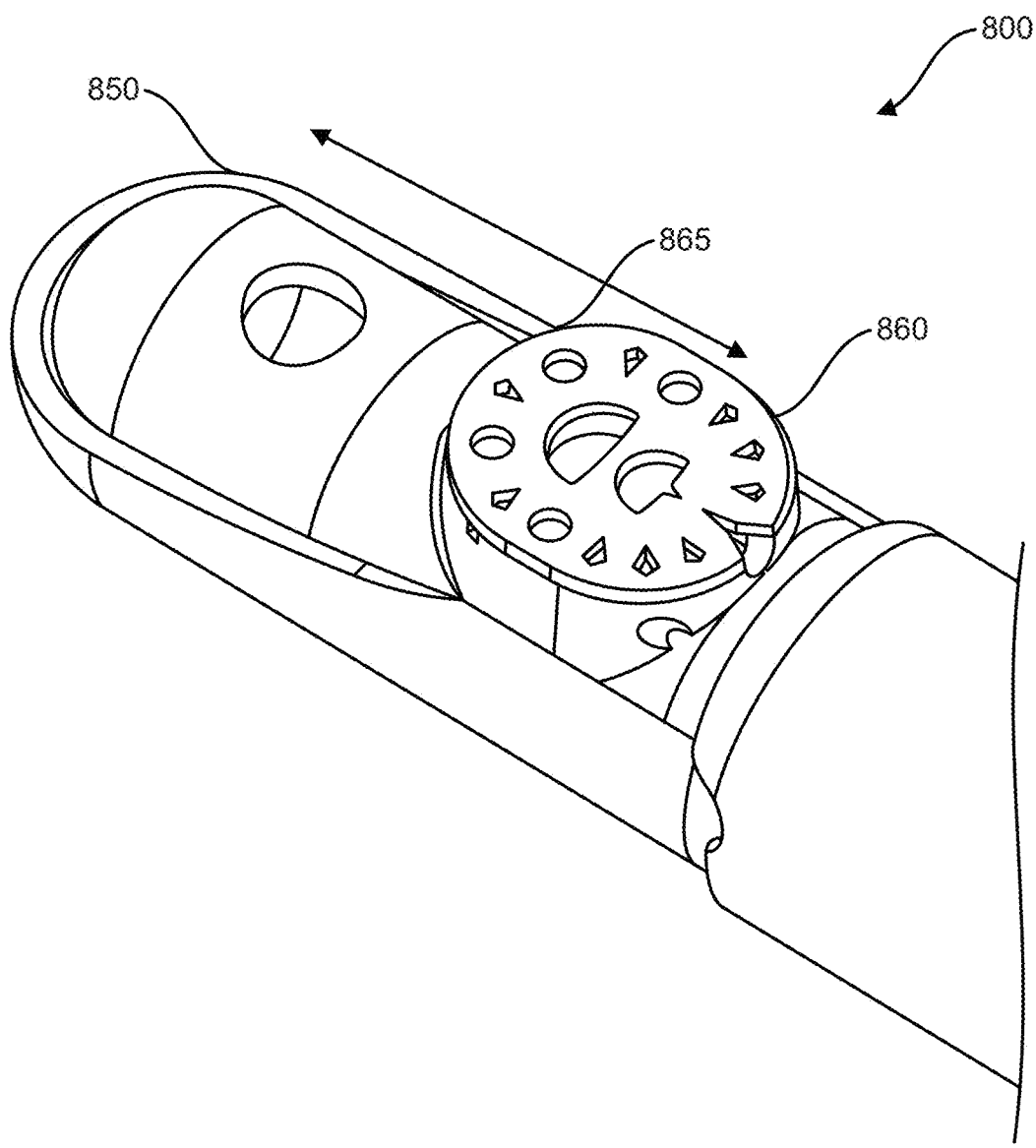
FIG. 8 shows an alternative embodiment of a blade distal tip, in accordance with the present disclosure.

A further alternative embodiment of a blade distal portion 800 may be seen in FIG. 8. This embodiment may include an axially slideable electrode 860 that may be removed from the immediate area around the distal tip during mechanical resection and subsequently slid over an aspiration aperture 850 when electrosurgical tissue treatment is desired. Multiple suction holes 865 are shown in this embodiment as well as others previously that may provide alternate suction paths to mitigate clogs.

The combination device may be operated in a variety of modes. For example in a first mechanical resection mode, the MDU 112 may rotate or move inner sleeve 410 so as to mechanically cut tissue, similar to other shaver devices. During this mode, resected tissue may be removed from the patient via opening 420 and along a lumen in the inner sleeve coupled to an aspiration source. Aspiration may be controlled by an aspiration controller 220, which may for example control a speed or rotation of a peristaltic pump. Alternatively a vacuum source may be coupled to aspiration tubing and the aspiration controller may move a pinch element or selectively close a valve. Alternatively the aspiration controller may include a movable construct having a first body having one or more apertures, and a second body having one or more apertures, whereby one or more of the first and second bodies is movable relative to the other such that alignment between the first and second body apertures can be varied to change the flow rate. Aspiration may be controlled at a first flow rate during resection, and this first flow rate may be adjustable either by the user or automatically, depending on a variety of parameters such as motor speed settings, sensed electrical parameters associated with the MDU, and temperature associated with the device, as way of non-limiting examples.

In a second mode, an electrosurgical mode, the inner sleeve 410 may be stationary, and window 420 may be facing lateral opening 330 so as to provide an aspiration conduit during electrosurgical treatment such as ablation or coagulation, or a combination of both. During this second mode, active electrode 360 may be placed adjacent a target tissue and the RF generator activated, so as to electrosurgically treat tissue. Fluid, tissue and/or plasma by-products may concomitantly be removed, along a path including through an opening 362 in the active electrode 362, through spacer opening 472, through inner sleeve opening 420 and along inner sleeve 410. Aspiration may be controlled by an aspiration control system such as a peristaltic pump or a device with controls a size of a fluid conduit or aperture in communication with the inner sleeve aspiration lumen. Aspiration control system may be in communication with RF generator. Communication may be wireless. Aspiration may be adjusted by user, or automatically set and adjusted based on operational parameters such as power settings on the RF generator, or based on sensed parameters such as electrode circuit impedance. Further description of this can be found in commonly assigned U.S. Pat. Nos. 8,192,424, 9,333,024 and 9,713,489 the complete disclosure of which is incorporated herein by reference. Aspiration may be adjusted via control of a pump speed associated with the aspiration controller, control of a valve position, or control of an orifice size as described earlier. In addition aspiration may be controlled by adjusting the position of opening 420 relative to opening 330, which may adjust the effective aspiration through the active electrode aperture versus through the aspiration conduit. Alternatively this second mode may be a coagulation mode that includes a lower voltage output configured to coagulate tissue rather than molecularly dissociate tissue.

Alternatively this second mode may include some concomitant coagulation with ablation of tissue. This may be achieved by modulating the output of the RF generator. Further description of this can be found in commonly assigned Patent application No. PCT/US18/032989 the complete disclosure of which is incorporated herein by reference. Alternatively this modulation may be achieved by pulsing aspiration, either through control of the aspiration control system such as the peristaltic pump, or by continued rotation of the inner sleeve while delivering RF. Controlled rotation of the inner sleeve may modulate aspiration through the active electrode aperture 362, which in turn may form and collapse plasma on the active electrode surface. Voltage supplied by the RF generator may a constant high frequency voltage level and sufficient to form plasma at the electrode surface while rotating the inner sleeve 410. For example, when the inner sleeve 410 is oriented so as to block the aspiration through the active electrode, a plasma would be formed on active electrodes surface providing ablation of tissue. When the inner sleeve 410 is oriented so as to draw fluid through the active electrode aperture 362, the energy supplied by the RF generator might not be sufficient to form plasma and therefore may provide a coagulation effect to the tissue. The rate at which the modulation of the aspiration rate occurs preferably is fast enough so that the tissue effect is perceived by the user as consistent, but slow enough to allow the plasma to intermittently form. The rotation of the blade could be continuous, or the blade could intermittently alternate between a number of positions that would affect the flow through the active electrode. So as to control or limit concomitant mechanical resection of tissue, the inner sleeve may preferably reciprocate so as that the cutting edge of the inner sleeve is not exposed through the outer sleeve cutting window and does not inadvertently mechanically cut tissue. Synchronized voltage modulation may also be added, between a first voltage sufficient to form a plasma and second that may aid the plasma to collapse with some communication between the inner sleeve orientation required.

During this concomitant mode a slower rotation speed than during mechanical resection may be preferable to control the frequency of plasma formation and collapse. The aspiration rate may be set at a first flowrate for a first configuration of active electrode, aspiration aperture therethrough and voltage supplied, such that when aspiration through the active electrode is at a maximum (when inner sleeve opening 425 directly faces the active electrode) plasma collapses and reduced aspiration (as the opening 425 rotates away from facing the active electrode underside) may allow plasma to reform. Alternatively aspiration flow rates may be more moderate for a second configuration of active electrode having aspiration aperture therethrough, and voltage may be supplied such that maximum moderate aspiration (when inner sleeve opening 425 directly faces the active electrode) aids in forming the plasma and lower aspiration rates (as the opening 425 rotates away from facing the active electrode underside) allows the plasma to collapse.

In a third combination mode, RF power may be supplied simultaneously while mechanically cutting tissue. The RF power may be supplied at a voltage sufficient to coagulate tissue, so as to improve visibility (reducing blood in the field). This may also reduce the need for the surgeon to stop and separately activate the RF generator when they see blood or need to ablate tissue. Alternatively if a more aggressive cutting is desired, RF power may be supplied sufficient to ablate tissue concomitantly while mechanically resecting tissue. In this third mode, should a more consistent plasma formation be desired, a separate aspiration conduit for the electrodes, distinct from the inner sleeve lumen may be preferable to maintain a more consistent fluid aspiration rate and thereby a more consistent plasma formation. Aspiration may be controlled by two aspiration controllers or at least two pumps associated with a single controller, a first pump controlled based on input from the MDU control, and second in response to input from the RF generator. Aspiration may be adjusted by user, or automatically set and adjusted based on operational parameters such as power settings on the MDU controller and/or RF generator, or based on sensed parameters such as electrode circuit impedance. Further description of this can be found in commonly assigned U.S. Pat. Nos. 8,192,424, 9,333,024 and 9,713,489 the complete disclosure of which is incorporated herein by reference.

Figure 9A:
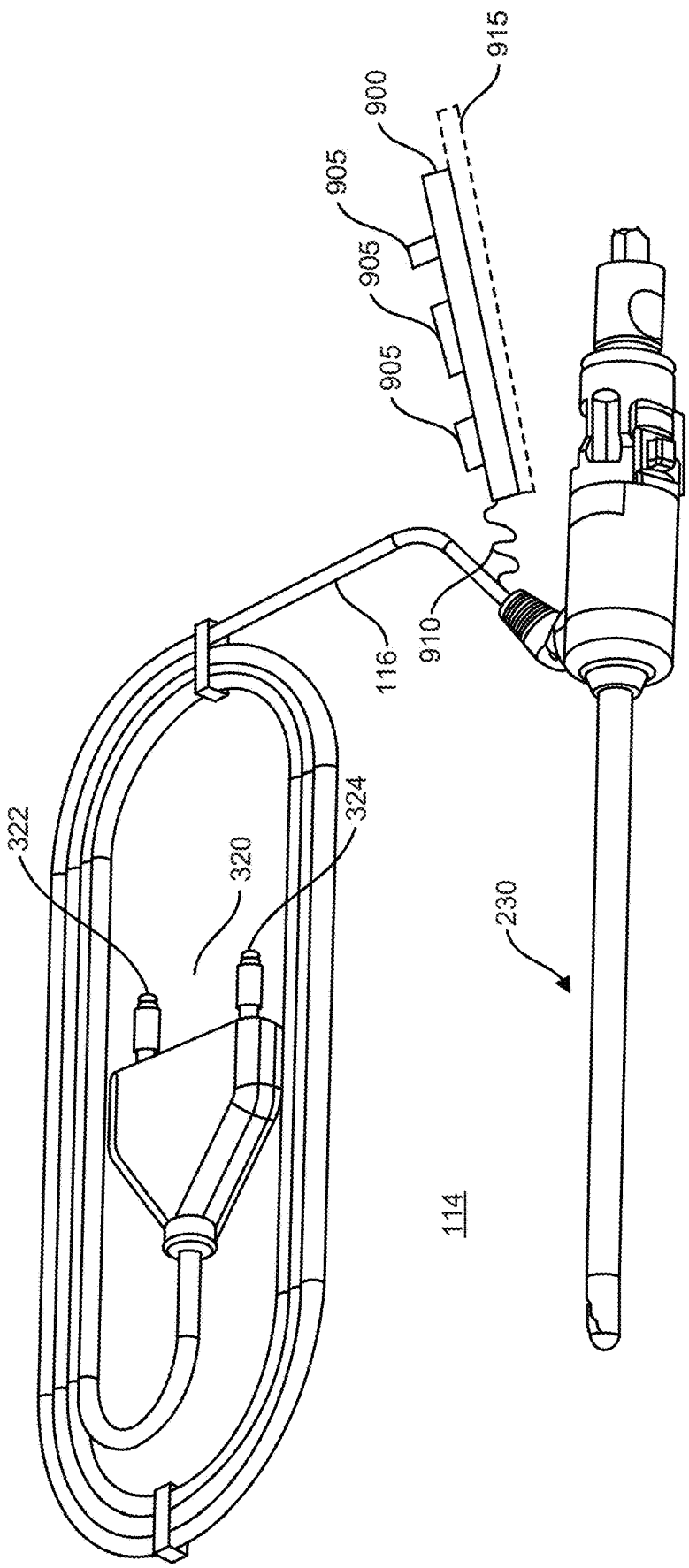
FIGS. 9A and 9B show an embodiment of a combination surgical device having a disposable switch, in accordance with the present disclosure.
Figure 9B:
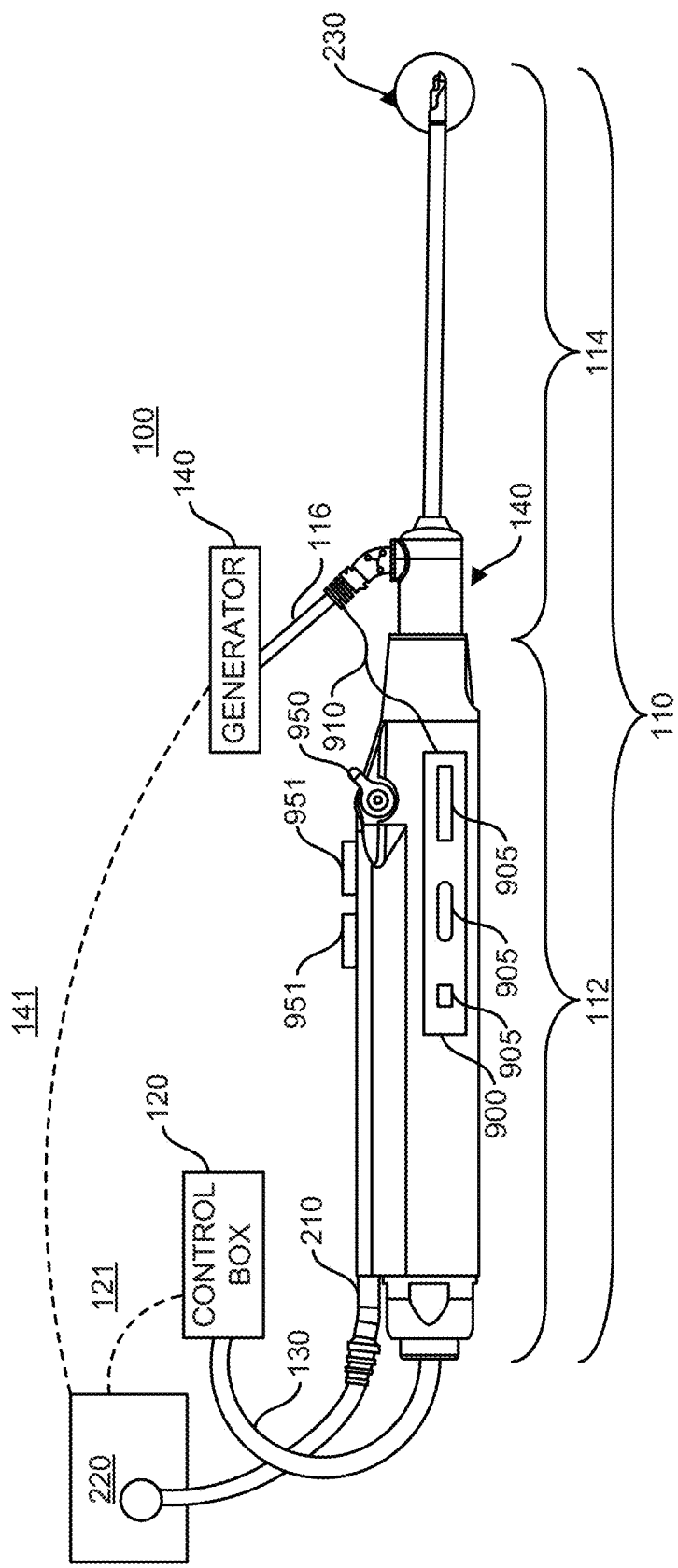

Now referring to FIGS. 9A and 9B, showing an embodiment that includes a blade portion 114 including a disposable handswitch 900, with buttons and controls 905 for use with a combination surgical device. Like components are given like numbering to previous figures. Since the reusable handle 112 may be alternatively used with non-combination devices that provide powered resection alone, a combination device including a second modality may require a control means that is not available via the reusable handle 112. One option, described heretoforth is the use of a footswitch. An alternate option, sometimes preferred by users is the provision for a handswitch option 900, that may be attached to the handle of a reusable device (shown in FIG. 9B) such as the combination surgical device for control of (RF) radiofrequency treatment. This may be in the form of RF generator control buttons 905 electrically coupled to the RF generator (140) via the RF generator cable 116. On opening the disposable package including the blade portion 114 with a handswitch 900, the user may couple the blade portion 112 to the handle 112 and then place the disposable handswitch 900 on a desired portion of the reusable handle 112. Disposable handswitch 900 may be removeably fixed to the MDU 112 using coupling means such as adhesive, or a clip that at least partially surrounds the MDU 112 for example. Coupling means may be operable to prevent unintentional relative movement between the handswitch 900 and reusable handle 112. Once the procedure is complete, the disposable handswitch 900 may be removed along with the blade portion 114 for disposal.

In one example embodiment, the inventor envisions a single strip of buttons 905 overmolded or placed within a rubber or elastomeric mat. Buttons 905 are operable to close an electric circuit or a pair of contacts upon activation of said button 905 to allow electrical energy to be delivered between the electrodes of the blade portion 114. A cord 910 or more preferably an extension of the overmolded rubber mat may physically couple the disposable blade 114 with the buttons 905. Cord 910 may house wiring for selective electrical communication between the blade 114 and generator cable 116 and may also electrically insulates the wires. Handswitch 900 may be couple to any portion of the blade portion 114 and the cord 910 may be long enough or extendable, allowing the handswitch 900 to attach to the reusable handle 112. The handswitch 900 may attach to the reusable handle 112 using an adhesive or sticky strip, which may be covered while packaged, covered by an easy to peel adhesive cover 915. Removal of this easy peel cover may then expose the adhesive to then attach the handswitch mat 900 to the handle 112.

The blade portion 114 is shown coupled to the reusable handle in FIG. 9B, the adhesive cover is removed and the handswitch strip attached to a desired location of the reusable handle 112. It may be preferable to attach the handswitch 900 to a side perpendicular to the side of the reusable permanent buttons 950 and 951 may be best. The inventor also envisions a 'Y" shaped strip allowing buttons to be placed on 2 opposing sides of the permanent buttons 951, giving the surgeon more options. The disposable handswitch 900 strip should be shaped to fit easily on an existing surface of the reusable handle 112, but does not need to be rectangular as shown. The disposable handswitch 900 strip is configured to attach to apportion of the device that is easy accessible by the user. The buttons 910 may include a first button to activate ablation, a second to activate coagulation, and maybe a third to cycle through power settings or different modes, such as a vacuum mode described in more detailed in commonly assigned U.S. Pat. Nos. 8,192,424, 9,333,024 and 9,713,489 the complete disclosure of which is incorporated herein by reference. The adhesive should allow strong attachment to the reusable MDU handle 112 and also provide for easy release at the end of the procedure. The adhesive is therefore configured to have a degree of water resistance to prevent peeling off during operating procedures.

In alternative embodiments, handswitch 900 may include a clip for selectively or temporarily fixing the handswitch 900 to the reusable handle 112. Clip may partially encircle the reusable handle 112. Clip may have an inner circumferential surface configured to engage an outer surface of the reusable handle 112, and may have an internal diameter slightly smaller than an outer diameter of the reusable handle 112, so as to better secure the handswitch 900. Alternatively or in addition to, inner surface of the clip may have gripping features, such as teeth or high friction surfaces to again improve engagement between the handswitch 900 and handle 112. Handswitch 900 may include 2 clips, one at either end of the handswitch 900 to better stabilize the handswitch 900 with the reusable handle 112.

In further alternative embodiments, handswitch 900 may include thin sleeve that may slide onto reusable handle, the sleeve having openings for access to the reusable controls 950 and 951. Alternatively, the handswitch 900 may include a thin wrapping element that is configured to wrap around a portion of the reusable handle and may include openings to expose the reusable controlled 950 and 950. The example wrap may completely wrap around the handle 112 and couple to itself using friction, Velcro or adhesive for example. The thin wrapping element may be partially stretchable to improve securement with the reusable handle.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A combination medical device for removing and treating tissue in a patient, comprising:
   a handle portion and a blade portion, the blade portion comprising an outer sleeve having a lumen with an inner shaft disposed therein, the outer sleeve having a window with a cutting edge, configured to mechanically cut tissue when the inner shaft rotates;
   wherein the outer sleeve defines an exposed electrically conductive portion with a lateral opening therethough, the lateral opening circumferentially spaced from and coextensive with the window, the exposed electrically conductive portion defining a return electrode; and
   wherein a dielectric spacer is coupled to the outer sleeve and extends through the lateral opening; and wherein the dielectric spacer includes a cavity that nests an active electrode and electrically isolates the active electrode from the return electrode.

2. The combination medical device of claim 1 wherein the dielectric spacer is a ceramic.

3. The combination medical device of claim 1 wherein the lateral opening defines a peripheral edge having a plurality of retention elements, configured to integrate with cooperating retention elements on the dielectric spacer.

4. The combination medical device of claim 1 wherein the dielectric spacer further comprises a circumferential overhang for partially wrapping around an outer surface of the outer sleeve.

5. The combination medical device of claim 1 wherein the inner shaft has a lumen that forms part of a fluid aspiration element, configured to remove tissue drawn through the window while mechanically resecting tissue and also configured to remove fluid and plasma by-products drawn through the active electrode while the device electrosurgically treats tissue.

6. The combination medical device of claim 1 wherein the active electrode has an aspiration opening therethrough for removing fluid and tissue debris.

7. The combination medical device of claim 1 wherein the blade portion further comprises an electrical switch assembly in electrical communication with the active electrode, the switch including attachment means for selective attachment of the switch assembly to a desired location on the handle portion.

8. The combination medical device of claim 7 wherein the switch assembly comprises a flexible substrate having first and second opposing sides, a button on the second side of the flexible substrate, and an electrically conductive element operably connected to said button for selectively coupling the at least one electrode with an output of an electrosurgical generator.

9. The combination medical device of claim 7 wherein the switch assembly attachment means is selected from the group consisting of an adhesive, a clip, a sleeve, a wrap.

10. The combination medical device of claim 1 wherein the dielectric spacer defines an aspiration aperture that extends through the lateral opening.

11. The combination medical device of claim 10 wherein the active electrode defines an aspiration aperture that is in fluid communication with the dielectric spacer aspiration aperture.

12. The combination medical device of claim 11 wherein the active electrode aspiration aperture is coextensive with a window of the inner shaft.

13. The combination medical device of claim 1 wherein the dielectric spacer includes a boss defining an aspiration opening, the boss configured to increase a distance between the active electrode and an internal surface of the return electrode.

14. The combination medical device of claim 1 wherein the lateral opening is circumferentially offset and radially opposite the window.

15. The combination medical device of claim 1 wherein the window is on a first side of the outer sleeve and the active electrode is disposed on a second side of the outer sleeve, the second side opposite the first side.

16. The combination medical device of claim 1 wherein the outer sleeve is formed of an electrically conductive tube and wherein the exposed electrically conductive portion defining the return electrode is an outer surface of the electrically conductive tube.

17. The combination medical device of claim 1 wherein the dielectric spacer cavity includes bilateral overhangs configured to constrain the active electrode.

18. The combination medical device of claim 1 wherein an outer circumferential surface of the active electrode is disposed radially farther than an outer circumferential surface of the return electrode.

19. The combination medical device of claim 1 wherein the lateral opening extends through the outer sleeve on a first circumferential side of the outer sleeve and the window extends through outer sleeve on an opposing circumferential side of the outer sleeve, and wherein the entire dielectric spacer is disposed on the first circumferential side.

20. The combination medical device of claim 1 wherein the dielectric spacer extends through the lateral opening up to the outer sleeve lumen.

* * * * *